US012163173B2

United States Patent
Alfonta et al.

(10) Patent No.: US 12,163,173 B2
(45) Date of Patent: Dec. 10, 2024

(54) **HIGHLY EFFICIENT AND TUNABLE SYSTEM FOR THE INCORPORATION OF UNNATURAL AMINO ACIDS INTO PROTEINS IN *ESCHERICHIA COLI***

(71) Applicants: B. G. NEGEV TECHNOLOGIES AND APPLICATIONS LTD., AT BEN-GURION UNIVERSITY, Beer Sheva (IL); REGENTS OF THE UNIVERSITY OF MINNESOTA, Minneapolis, MN (US)

(72) Inventors: Lital Alfonta, Omer (IL); Vincent Noireaux, Minneapolis, MN (US); Orr Schlesinger, Beer-Sheva (IL); Yonatan Chemla, Beer-Sheva (IL); Eden Ozer, Rishon Lezion (IL)

(73) Assignees: B. G. NEGEV TECHNOLOGIES AND APPLICATIONS LTD., AT BEN-GURION UNIVERSITY, Beer Sheva (IL); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1290 days.

(21) Appl. No.: 16/347,880

(22) PCT Filed: Nov. 9, 2017

(86) PCT No.: PCT/IL2017/051221
§ 371 (c)(1),
(2) Date: May 7, 2019

(87) PCT Pub. No.: WO2018/087760
PCT Pub. Date: May 17, 2018

(65) Prior Publication Data
US 2019/0330672 A1 Oct. 31, 2019

Related U.S. Application Data

(60) Provisional application No. 62/420,010, filed on Nov. 10, 2016.

(51) Int. Cl.
*C12P 21/02* (2006.01)
*C12N 15/67* (2006.01)

(52) U.S. Cl.
CPC .............. *C12P 21/02* (2013.01); *C12N 15/67* (2013.01); *C12N 2330/51* (2013.01)

(58) Field of Classification Search
CPC ...... C12P 21/02; C12N 15/67; C12N 2330/51
See application file for complete search history.

(56) References Cited

U.S. PATENT DOCUMENTS

2016/0312215 A1* 10/2016 Murray .................. C12N 15/64

FOREIGN PATENT DOCUMENTS

WO  WO-2015193897 A1 * 12/2015 ..... C12Y 601/01001

OTHER PUBLICATIONS

Kipper K, et al. Application of Noncanonical Amino Acids for Protein Labeling in a Genomically Recoded *Escherichia coli*. ACS Synth Biol. Oct. 24, 2016.233-255 (Year: 2016).*
Terpe K. Overview of bacterial expression systems for heterologous protein production: from molecular and biochemical fundamentals to commercial systems. Appl Microbiol Biotechnol. Sep. 2006; 72(2):211-22 (Year: 2006).*
Brewster, Robert C., et al. Tuning promoter strength through RNA polymerase binding site design in *Escherichia coli*. PLoS computational biology 8.12 (2012) (Year: 2012).*
Seo, S., Yang, JS., Cho, HS. et al. Predictive combinatorial design of mRNA translation initiation regions for systematic optimization of gene expression levels. Sci Rep 4, 4515 (2014) (Year: 2014).*
Lammers, Christoph, Liljan E. Hahn, and Heinz Neumann. "Optimized plasmid systems for the incorporation of multiple different unnatural amino acids by evolved orthogonal ribosomes." ChemBioChem 15.12 (2014): 1800-1804 (Year: 2014).*
Shin, G.Y.N Shin. (2012). Molecular programming with a transcription and translation cell-free toolbox: from elementary gene circuits to phage synthesis (Year: 2012).*
Chemla, Yonatan, et al. "Genetically expanded cell-free protein synthesis using endogenous pyrrolysyl orthogonal translation system." Biotechnology and bioengineering 112.8 ( Mar. 5, 2015): 1663-1672 (Year: 2015).*
Schlesinger (ACS synthetic biology 6.6 (Feb. 23, 2017): 1076-1085) (Year: 2017).*
O'Donoghue P et al., "Near-cognate suppression of amber, opal and quadruplet codons competes with aminoacyl-tRNAPyl for genetic code expansion", FEBS Letters, Nov. 2, 2012;586(21):3931-7.
Pavlov M., et al., "A Direct Estimation of the Context Effect on the Efficiency of Termination." Journal of Molecular Biology, Dec. 4, 1998; 284(3):579-90.
Kipper, K., et al., "Application of noncanonical amino acids for protein labeling in a genomically recoded *Escherichia coli*." ACS Synthetic Biology, 6(2), 233-255 (2016).
Terpe, K. "Overview of bacterial expression systems for heterologous protein production: from molecular and biochemical fundamentals to commercial systems." Applied Microbiology and Biotechnology, 72(2), 211-222 (2006).

(Continued)

*Primary Examiner* — Nancy J Leith
*Assistant Examiner* — Kyle T Rega
(74) *Attorney, Agent, or Firm* — The Roy Gross Law Firm, LLC; Roy Gross

(57) ABSTRACT

The present invention provides a composition with a cell having an orthogonal translation system, and an expression vector. The invention also provides a method of producing a protein carrying an unnatural amino acid, and a kit for use in producing a protein carrying the unnatural amino acid.

19 Claims, 11 Drawing Sheets

Specification includes a Sequence Listing.

(56) References Cited

OTHER PUBLICATIONS

Brewster, R. C., et al., "Tuning Promoter Strength through RNA Polymerase Binding Site Design in *Escherichia Coli*." PLoS Computational Biology, 8(12), e1002811 (2012).

Handy, D. E., et al., "Homocysteine Down-regulates Cellular Glutathione Peroxidase (GPx1) by Decreasing Translation." Journal of Biological Chemistry, 280 (16), 15518-15525 (2005).

Monk, J. W., et al., "Rapid and Inexpensive Evaluation of Nonstandard Amino Acid Incorporation in *Escherichia Coli*." ACS Synthetic Biology, 6(1), 45-54 (2016).

Dehli, T., et al., "Tunable Promoters in Synthetic and Systems Biology." In Reprogramming Microbial Metabolic Pathways (pp. 181-201) (2012).

Chemla Y, et al., "Genetically Expanded Cell-Free Protein Synthesis using Endogenous Pyrrolysyl Orthogonal Translation System." Biotechnology and Bioengineering (2015), 112(8):1663-72.

Jackson JC, et al., "Improving Nature's Enzyme Active Site with Genetically Encoded Unnatural Amino Acids." Journal of the American Chemical Society 128:11124-7 (2006).

Wang L., et al., "Expanding the genetic code of *Escherichia coli*." Science 292:498-500 (2001).

Wang L., et al., "A general approach for the generation of orthogonal tRNAs." Chemistry & Biology 8:883-90 (2001).

Browning, D.F., et al., "The Regulation of Bacterial Transcription Initiation." Nature Reviews Microbiology 2, 57-65, (2004).

Cannarozzi, G., et al., "A Role for Codon Order in Translation Dynamics." Cell 141, 355-367 (2010).

Ellis, R.J., "Macromolecular crowding: obvious but underappreciated." Trends in Biochemical Sciences vol. 26, 597-604 (2001).

Fan, C., et al., "Rationally evolving tRNAPyl for efficient incorporation of noncanonical amino acids." Nucleic Acids Research 43, e156 (2015).

Jin, H., et al., "Cis control of gene expression in *E.coli* by ribosome queuing at an inefficient translational stop signal." EMBO J. 21, 4357-4367, (2002).

Klumpp, S., et al., "Stochasticity and traffic jams in the transcription of ribosomal RNA: Intriguing role of termination and antitermination." Proceedings of the National Academy of Sciences 105, 18159-18164, (2008).

Mitarai, N., et al. "Control of ribosome traffic by position-dependent choice of synonymous codons." Phys. Biol. 10, 056011 (2013).

Tan, C., et al., "Molecular crowding shapes gene expression in synthetic cellular nanosystems." Nature Nanotechnology 8, 602-608 (2013).

Wang, J., et al., "Kinetics of tRNA Pyl-Mediated Amber Suppression in *Escherichia Coli* Translation Reveals Unexpected Limiting Steps and Competing Reactions." Biotechnology and Bioengineering (2015).

International Search Report, International Application No. PCT/IL2017/051221, dated Dec. 25, 2017.

\* cited by examiner

```
                             SEQUENCE LISTING

<160> NUMBER OF SEQ ID NOS: 20

<210> SEQ ID NO 1
<211> LENGTH: 55
<212> TYPE: DNA
<213> ORGANISM: artificial
<220> FEATURE:
<223> OTHER INFORMATION: synthetic

<400> SEQUENCE: 1
tgagctaaca ccgtgcgtgt tgacaatttt acctctggcg gtgataatgg ttgca         55

<210> SEQ ID NO 2
<211> LENGTH: 6
<212> TYPE: DNA
<213> ORGANISM: artificial
<220> FEATURE:
<223> OTHER INFORMATION: synthetic

<400> SEQUENCE: 2 gctagc                                                                6

<210> SEQ ID NO 3
<211> LENGTH: 33
<212> TYPE: DNA
<213> ORGANISM: artificial
<220> FEATURE:
<223> OTHER INFORMATION: synthetic

<400> SEQUENCE: 3
aataattttg tttaacttta agaaggagat ata                                 33

<210> SEQ ID NO 4
<211> LENGTH: 94
<212> TYPE: DNA
<213> ORGANISM: artificial
<220> FEATURE:
<223> OTHER INFORMATION: synthetic

<400> SEQUENCE: 4
tgagctaaca ccgtgcgtgt agacaatttt acctctggcg gtgataatgg ttgcagctag    60
caataatttt gtttaacttt aagaaggaga tata                                94

<210> SEQ ID NO 5
<211> LENGTH: 94
<212> TYPE: DNA
<213> ORGANISM: artificial
<220> FEATURE:
<223> OTHER INFORMATION: synthetic

<400> SEQUENCE: 5
tgagctaaca ccgtgcgtgt tgacaatttt acctctggcg gtgataatgg ttgcagctag    60
caataatttt gtttaacttt aagaacgaga tata                                94

<210> SEQ ID NO 6
<211> LENGTH: 708
<212> TYPE: DNA
<213> ORGANISM: artificial
<220> FEATURE:
```

<223> OTHER INFORMATION: synthetic

<400> SEQUENCE: 6

| | | | | | |
|---|---|---|---|---|---|
| atggagcttt | tcactggcgt | tgttcccatc | ctggtcgagc | tggacggcga | cgtaaacggc | 60 |
| cacaagttca | gcgtgtccgg | cgagggcgag | ggcgatgcca | cctacggcaa | gctgaccctg | 120 |
| aagttcatct | gcaccaccgg | caagctgccc | gtgccctggc | ccaccctcgt | gaccaccctg | 180 |
| acctacggcg | tgcagtgctt | cagccgctac | cccgaccaca | tgaagcagca | cgacttcttc | 240 |
| aagtccgcca | tgcccgaagg | ctacgtccag | gagcgcacca | tcttcttcaa | ggacgacggc | 300 |
| aactacaaga | cccgcgccga | ggtgaagttc | gagggcgaca | ccctggtgaa | ccgcatcgag | 360 |
| ctgaagggca | tcgacttcaa | ggaggacggc | aacatcctgg | ggcacaagct | ggagtacaac | 420 |
| tacaacagcc | acaacgtcta | tatcatggcc | gacaagcaga | agaacggcat | caaggtgaac | 480 |
| ttcaagatcc | gccacaacat | cgaggacggc | agcgtgcagc | tcgccgacca | ctaccagcag | 540 |
| aacaccccca | tcggcgacgg | ccccgtgctg | ctgcccgaca | accactacct | gagcacccag | 600 |
| tccgccctga | gcaaagaccc | caacgagaag | cgcgatcaca | tggtcctgct | ggagttcgtg | 660 |
| accgccgccg | ggatctctag | agtgcaccac | caccaccatc | acgtgtaa | | 708 |

<210> SEQ ID NO 7
<211> LENGTH: 31
<212> TYPE: DNA
<213> ORGANISM: artificial
<220> FEATURE:
<223> OTHER INFORMATION: synthetic

<400> SEQUENCE: 7
gcgatgccac ctagggcaag ctgaccctga a       31

<210> SEQ ID NO 8
<211> LENGTH: 31
<212> TYPE: DNA
<213> ORGANISM: artificial
<220> FEATURE:
<223> OTHER INFORMATION: synthetic

<400> SEQUENCE: 8
ttcagggtca gcttgcccta ggtggcatcg c       31

<210> SEQ ID NO 9
<211> LENGTH: 35
<212> TYPE: DNA
<213> ORGANISM: artificial
<220> FEATURE:
<223> OTHER INFORMATION: synthetic

<400> SEQUENCE: 9
ccccgtgctg ctgccctaga accactacct gagca       35

<210> SEQ ID NO 10
<211> LENGTH: 35
<212> TYPE: DNA
<213> ORGANISM: artificial
<220> FEATURE:
<223> OTHER INFORMATION: synthetic

<400> SEQUENCE: 10
tgctcaggta gtggttctag ggcagcagca cgggg       35

<210> SEQ ID NO 11
<211> LENGTH: 37

<212> TYPE: DNA
<213> ORGANISM: artificial
<220> FEATURE:
<223> OTHER INFORMATION: synthetic

<400> SEQUENCE: 11
tgcagctcgc cgaccactag cagcagaaca cccccat                              37

<210> SEQ ID NO 12
<211> LENGTH: 37
<212> TYPE: DNA
<213> ORGANISM: artificial
<220> FEATURE:
<223> OTHER INFORMATION: synthetic

<400> SEQUENCE: 12
atgggggtgt tctgctgcta gtggtcggcg agctgca                              37

<210> SEQ ID NO 13
<211> LENGTH: 35
<212> TYPE: DNA
<213> ORGANISM: artificial
<220> FEATURE:
<223> OTHER INFORMATION: synthetic

<400> SEQUENCE: 13
gctaacaccg tgcgtgtaga caattttacc tctgg                                35

<210> SEQ ID NO 14
<211> LENGTH: 35
<212> TYPE: DNA
<213> ORGANISM: artificial
<220> FEATURE:
<223> OTHER INFORMATION: synthetic

<400> SEQUENCE: 14
ccagaggtaa aattgtctac acgcacggtg ttagc                                35

<210> SEQ ID NO 15
<211> LENGTH: 36
<212> TYPE: DNA
<213> ORGANISM: artificial
<220> FEATURE:
<223> OTHER INFORMATION: synthetic

<400> SEQUENCE: 15
ttgtttaact ttaagaacga gatataccat ggagct                               36

<210> SEQ ID NO 16
<211> LENGTH: 36
<212> TYPE: DNA
<213> ORGANISM: artificial
<220> FEATURE:
<223> OTHER INFORMATION: synthetic

<400> SEQUENCE: 16
agctccatgg tatatctcgt tcttaaagtt aaacaa                               36

<210> SEQ ID NO 17
<211> LENGTH: 20
<212> TYPE: DNA
<213> ORGANISM: artificial
<220> FEATURE:
<223> OTHER INFORMATION: synthetic

<400> SEQUENCE: 17

```
atgaagcagc acgacttctt                                           20

<210> SEQ ID NO 18
<211> LENGTH: 21
<212> TYPE: DNA
<213> ORGANISM: artificial
<220> FEATURE:
<223> OTHER INFORMATION: synthetic

<400> SEQUENCE: 18
gtggctgttg tagttgtact c                                         21

<210> SEQ ID NO 19
<211> LENGTH: 18
<212> TYPE: DNA
<213> ORGANISM: artificial
<220> FEATURE:
<223> OTHER INFORMATION: synthetic

<400> SEQUENCE: 19
cggtgaatac gttcccgg                                             18

<210> SEQ ID NO 20
<211> LENGTH: 19
<212> TYPE: DNA
<213> ORGANISM: artificial
<220> FEATURE:
<223> OTHER INFORMATION: synthetic

<400> SEQUENCE: 20
ggttaccttg ttacgactt                                            19
```

HIGHLY EFFICIENT AND TUNABLE SYSTEM FOR THE INCORPORATION OF UNNATURAL AMINO ACIDS INTO PROTEINS IN *ESCHERICHIA COLI*

CROSS-REFERENCE TO RELATED APPLICATIONS

This application is a National Phase of PCT Patent Application No. PCT/IL2017/051221 having International filing date of Nov. 9, 2017, which claims the benefit of priority of U.S. Provisional Patent Application No. 62/420,010, filed on Nov. 10, 2016. The contents of the above applications are all incorporated by reference as if fully set forth herein in their entirety.

REFERENCE TO AN ELECTRONIC SEQUENCE LISTING

The contents of the electronic sequence listing (SQL.txt; Size: 4,933bytes; and Date of Creation: May 7, 2019) is herein incorporated by reference in its entirety.

FIELD OF INVENTION

The present invention is directed to the field of genetic code expansion and novel protein engineering.

BACKGROUND OF THE INVENTION

Incorporation of unnatural amino acids (UAAs) into proteins is a rapidly developing and increasingly employed technology that uses the expansion of the genetic code of an organism to introduce novel and unique chemical properties into a protein of choice. This technology allows site specific incorporation, into a target protein, of a synthetic amino acid with unique chemical, biological or physical properties, thus creating novel tools for protein engineering. The most widely used method for UAA incorporation makes use of nonsense (stop) codons suppression, essentially transforming them to sense codons encoding for the incorporation of a UAA. This recoding is made possible by introducing orthogonal translational components, consisting of an orthogonal tRNA that has an anticodon that corresponds to a stop codon (o-tRNA) and an orthogonal amino-acyl-tRNA synthetase (o-aaRS) that recognizes only the UAA and the tRNA introduced to the system (Wang L and Shultz P G, Chemistry and Biology 2001, 8:883-90). These two components are termed orthogonal translation system (OTS).

The most common OTS uses the host organism's endogenous protein synthesis system for the incorporation of the UAA as a response to the 'amber' (UAG) stop codon inserted in the site chosen for the UAA incorporation. This common genetic code expansion methodology is widely used and has been the subject of multiple efforts of improvement and optimization (Neumann H, Federation of European Biochemical Societies Letters 2012, 586: 2057-64). However, constraints on protein yields and efficiency often limit various applications for this method. Suppression efficiency of each developed set of OTS depends on its ability to compete with the endogenous release factor (RF) that terminates the translation process, thus reducing the yields of expression of the protein. Another limitation of the system is the undesired non-specific incorporation (or read-through) of a natural amino acid into the suppression site (Harrell L, et al. Nucleic Acids Research 2002, 30: 2011-7; O'Donoghue P, et al. Federation of European Biochemical Societies Letters 2012, 586: 3931-7; Pavlov M Y, et al. Journal of Molecular Biology 1998, 284: 579-90).

The other factor which affects protein yields is the expression vector, which contains the gene of interest under regulation of various promoters. In order to achieve high protein yields, most developed systems make use of bacteriophage RNA polymerases (RNAP) and promoters such as T7 for transcription of the recombinant genes. Bacteriophage RNAP are the most efficient for transcription, but they also have some limitations such as not always replacing *E. coli* endogenous RNAP. Additionally, using highly efficient promoters in-vivo is often toxic to the host organism due to an over-expression of the target protein. A system with high fidelity and large protein yield is thus still elusive.

SUMMARY OF THE INVENTION

The present invention provides a composition of a cell comprising an orthogonal translation system and an expression vector. The invention also provides a method of producing a protein containing an unnatural amino acid, and a kit for use in producing a protein containing an unnatural amino acid.

According to the first aspect, there is provided a cell, comprising:
a) an orthogonal translation system comprising an orthogonal tRNA that has an anticodon that corresponds to a stop codon (o-tRNA) and an unnatural amino acid (UAA)-specific orthogonal amino-acyl-tRNA synthetase (o-aaRS),
b) a vector comprising, a promoter region operably linked to an open reading frame, wherein said promoter region has a transcriptional initiation rate between 1.0 and 10 mRNAs per second and/or a ribosome initiation rate between 1.0 and 4.5 ribosomes per second and said open reading frame comprises and at least one of the stop codon within: (i) the first 240 bases; or (ii) the first third of the open reading frame.

According to one embodiment, the UAA is Proparagyl-1-Lysine (PrK).

According to one embodiment, the codon is a TAG stop codon, and the cell is devoid of release factor 1 (RF1) expression and further comprises an endogenous genome devoid of TAG stop codons.

According to one embodiment, the cell is a genomically recoded *E. coli* (GRO) strain and the stop codon is a TAG stop codon.

According to one embodiment, the promoter region comprises OR2-OR1-Pr promoter region.

According to another aspect, there is provided a method for producing a protein comprising an UAA, comprising:
a) providing at least one cell;
b) expressing in the cell an orthogonal translation system comprising an orthogonal tRNA that has an anticodon that corresponds to a stop codon (o-tRNA) and an UAA-specific orthogonal amino-acyl-tRNA synthetase (o-aaRS);
c) expressing in the cell a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises at least one of the stop codon within: (i) the first 240 bases; or (ii) the first third of the open reading frame;
d) contacting the cell with the UAA, thereby producing the protein comprising the UAA.

According to one embodiment the UAA is Proparagyl-l-Lysine (PrK).

According to one embodiment, the stop codon is a TAG stop codon, and the cell is devoid of RF1 expression and TAG stop codons.

According to one embodiment, the cell is a genomically recoded E. coli (GRO) strain.

According to one embodiment, the promoter region comprises OR2-OR1-Pr promoter region.

According to another aspect, there is provided a kit comprising:

a) an orthogonal translation system comprising an orthogonal tRNA that has an anticodon that corresponds to a stop codon (o-tRNA) and an UAA-specific orthogonal amino-acyl-tRNA synthetase (o-aaRS);
b) a vector comprising, a promoter region operably linked to a multiple cloning site (MCS), wherein the promoter region has a transcriptional initiation rate between 1.0 and 10 mRNAs per second and/or a ribosome initiation rate between 1.0 and 4.5 ribosomes per second;
c) instructions for designing a nucleic acid molecule, wherein the nucleic acid molecule comprises at least one of the stop codon within: (i) the first 240 bases; or (ii) the first third of the open reading frame.

According to one embodiment, the promoter region comprises OR2-OR1-Pr promoter region.

According to one embodiment, the kit also comprises the UAA.

According to one embodiment, the stop codon is a TAG stop codon, and the kit further comprises a cell devoid of TAG stop codons and RF1 expression.

DETAILED DESCRIPTION OF THE INVENTION

Figure 1A:
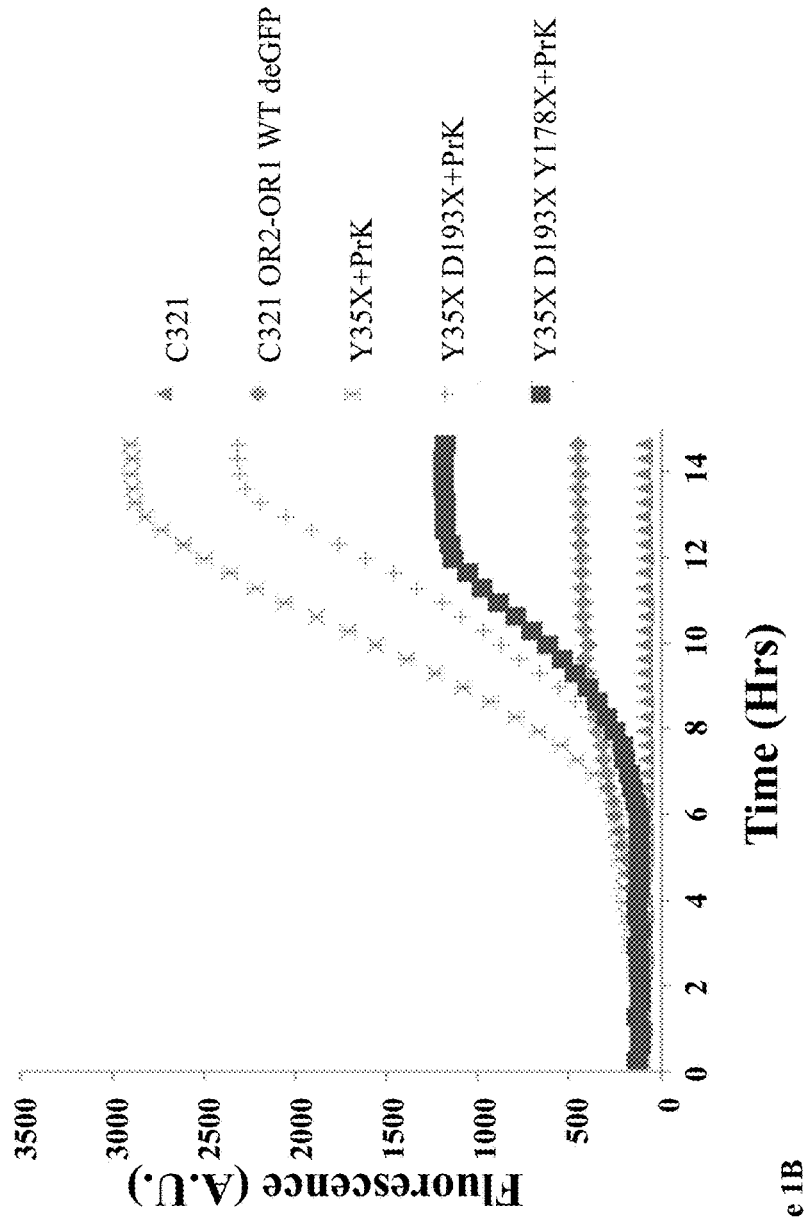
FIGS. 1A-C. Analysis of deGFP mutants using the OR2-OR1-PR promoter. (1A) A line graph depicting fluorescence of cells upon using the OR2-OR1-Pr promoter to express deGFP and deGFP containing one, two or three TAG stop codons in the presence or absence of PrK. (1B) An image of in gel fluorescence of different mutants after the conduction of a "click" reaction with azide-TAMRA reporter on a crude lysate. Image was taken using TAMRA fluorescent mode (Ex/Em 546/565 nm). Wild-type deGFP was used as control. (1C) An image of a Western blot image of the crude lysates from 1B using anti-deGFP-specific antibodies.

The present invention provides, in some embodiments, a method for integrating a UAA into a protein, a kit for doing the same, and a cell which is capable of producing a protein comprising a UAA. In one embodiment, a cell as described herein comprises an orthogonal translation system comprising an orthogonal tRNA, wherein the orthogonal tRNA comprises an anticodon that corresponds to a stop codon (o-tRNA) and an unnatural amino acid (UAA)-specific orthogonal amino-acyl-tRNA synthetase (o-aaRS), and a vector comprising, a promoter region operably linked to an open reading frame, wherein the promoter region has a transcriptional initiation rate between 1.0 and 10 mRNAs per second and a ribosome initiation rate between 1.0 and 4.5 ribosomes per second and the open reading frame comprises at least one of the stop codon located within: (i) the first 240 bases; or (ii) the first third of the open reading frame. In one embodiment, "the first" refers to the first 5' nucleotide.

In one embodiment, a cell as described herein comprises: UAA in the form of Proparagyl-l-Lysine (PrK), a TAG stop codon, an endogenous genome, a TAG stop codon, a promoter region comprising OR2-OR1-Pr promoter region, an unnatural amino acid, or any combination thereof In one embodiment, a cell as described herein is devoid of RF1 expression, devoid of a TAG stop codon, or both.

By one aspect, the present invention concerns a cell comprising: an orthogonal translation system comprising an orthogonal tRNA that has an anticodon that corresponds to a stop codon (o-tRNA) and an UAA-specific orthogonal amino-acyl-tRNA synthetase (o-aaRS), a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises at least one of the stop codon within either the first 240 bases or the first third of the open reading frame.

The term "cell" as used herein refers to any prokaryotic cell e.g., bacteria or protozoa. In some embodiments, the cell is an *E. coli* cell. In some embodiments, the cell is a solitary cell. In some embodiments, the cell is an organism consisting the cell. In some embodiments, the cell is genetically modified such that it's endogenous genome is devoid of all TAG stop codons. In some embodiments, the cell is genetically modified such that it is devoid of all release factor 1 (RF1) expression. In some embodiments, the cell is genetically modified such that it is devoid of all TAG stop codons and RF1 expression. In some embodiments, the cell is a eukaryotic cell. In some embodiments, the cell is a cell comprising a synthetic and/or engineered DNA molecule. In some embodiments, the cell is a cell comprising an unnatural amino acid.

In some embodiments, the cell is a cell comprising a synthetic vector and/or plasmid. In some embodiments, the cell is a cell comprising a mutated TAA stop codon. In some embodiments, the cell is a cell comprising a mutated stop codon. In some embodiments, the cell is a cell comprising an orthogonal tRNA synthetase. In some embodiments, the cell is a cell comprising an O-tRNA anticodon. In some embodiments, the cell is a cell contacted with an O-tRNA anticodon. In some embodiments, the cell is a cell contacted with an orthogonal amino-acyl-tRNA synthetase that recognizes only the UAA. In some embodiments, the cell is a cell comprising an orthogonal amino-acyl-tRNA synthetase that recognizes only the UAA. n some embodiments, the cell is a cell comprising a Propargyl-l-Lysine.

The term "codon" as used herein refers to the three-nucleotide sequence that is the genetic unit of DNA and RNA. A codon codes for a single amino acid, or for a stop to the addition of amino acids. A "stop codon" is thus a codon that codes for a stop to amino acid addition. Three stop codons exist in nature, the TAG, TGA and the TAA stop codons.

In some embodiments, all the endogenous TAG codons in the cell have been mutated to TAA codons. In some embodiments, all the endogenous TAG codons in the cell have been mutated to TGA stop codons. In some embodiments, all the endogenous TAG codons in the cell have been mutated to either a TAA stop codon or a TGA stop codon.

In some embodiments, the cell is genetically modified such that greater than 99%, greater than 95%, greater than 90%, greater than 85%, greater than 80%, or greater than 75% of its endogenous TAA stop codons have been mutated. Each possibility represents a separate embodiment of the present invention.

In some embodiments, the cell comprises an orthogonal translation system comprising an orthogonal tRNA that has an anticodon that corresponds to a stop codon (o-tRNA) and an UAA-specific orthogonal amino-acyl-tRNA synthetase (o-aaRS). In some embodiments, the stop codon is a UAG stop codon. In some embodiments, the cell comprises an endogenous genome devoid of all TAG stop codons, and an orthogonal translation system comprising an orthogonal tRNA that has an anticodon that corresponds to a UAG stop codon (o-tRNA) and an UAA-specific orthogonal amino-acyl-tRNA synthetase (o-aaRS).

The term "orthogonal" as used herein refers to molecules (e.g., "orthogonal tRNA synthetase" and "orthogonal tRNA" pairs) that can process information in parallel with wild-type molecules (e.g., tRNA synthetases and tRNAs), but that do not engage in crosstalk with the wild-type molecules of a cell. As a non-limiting example, the orthogonal tRNA synthetase preferentially aminoacylates a complementary orthogonal tRNA (O-tRNA), but no other cellular tRNAs, with a non-canonical amino acid (e.g., Propargyl-l-Lysine), and the orthogonal tRNA is a substrate for the orthogonal synthetase but is not substantially aminoacylated by any endogenous tRNA synthetases.

In the context of tRNAs and aminoacyl-tRNA synthetases, the term "orthogonal" refers to an inability or reduced efficiency, e.g., less than 20% efficiency, less than 10% efficiency, less than 5% efficiency, or less than 1% efficiency, of an O-tRNA to function with an endogenous tRNA synthetase (RS) compared to an endogenous tRNA to function with the endogenous tRNA synthetase, or of O-tRNA synthetase (O-RS) to function with an endogenous tRNA compared to an endogenous tRNA synthetase to function with the endogenous tRNA. For a non-limiting example, an O-tRNA in a cell is aminoacylated by any endogenous RS of the cell with reduced or even zero efficiency, when compared to aminoacylation of an endogenous tRNA by the endogenous RS. In another non-limiting example, an O-tRNA synthetase aminoacylates any endogenous tRNA a cell of interest with reduced or even zero efficiency, as compared to aminoacylation of the endogenous tRNA by an endogenous RS.

In some embodiments, the O-tRNA anticodon loop recognizes a codon, which is not recognized by endogenous tRNAs, on the mRNA and incorporates the UAA at this site in the polypeptide, details of which are further described, for example, in U.S. Pat. No. 2006/0160175, which is hereby incorporated by reference in its entirety. For a non-limiting example, the unique codon may include nonsense codons, such as, stop codons, four or more base codons, rare codons, codons derived from natural or unnatural base pairs and/or the like. In some embodiments, the unique codon is the TAG stop codon.

The term "unnatural amino acid" as used herein refers to any amino acid that is not genetically encoded for in an organism. The term "unnatural amino acid" as used herein refers to an amino acid that that is not inherently present within the organism. This refers to any amino acid other than the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Examples of unnatural amino acids are common in the art.

In some embodiments, the unnatural amino acid is Propargyl-l-Lysine (PrK).

The term "UAA-specific orthogonal amino-acyl-tRNA synthetase (o-aaRS)" refers to an orthogonal amino-acyl-tRNA synthetase that recognizes only the UAA and the tRNA introduced to the system of the invention.

In some embodiments, the orthogonal translation system is introduced into the cell by standard methods including electroporation (e.g., as described in From et al., Proc. Natl. Acad. Sci. USA 82, 5824 (1985)), infection by viral vectors, high velocity ballistic penetration by small particles with the nucleic acid either within the matrix of small beads or particles, or on the surface (Klein et al., Nature 327. 70-73 (1987)), and/or the like.

In some embodiments, the cell comprises a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises at least one stop codon within either the first 240 bases or the first third of the open reading frame.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid" which refers to a circular double stranded DNA loop into which additional DNA segments can be inserted, such as by standard molecular cloning techniques. Another type of vector, wherein virally-derived DNA or RNA sequences are present in the virus (e.g. retroviruses, replication defective retroviruses, adenoviruses, replication defective adenoviruses, and adeno-associated viruses). Viral vectors also include polynucleotides carried by a virus for transfecting into host cells. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". Common expression vectors of utility in recombinant DNA techniques are often in the form of plasmids.

Recombinant expression vectors or synthetic expression vectors can comprise a nucleic acid of the invention in a form suitable for expression of the nucleic acid in a host cell, which means that the recombinant expression vectors include one or more regulatory elements, which may be selected on the basis of the host cell to be used for expression, that is operatively-linked to the nucleic acid sequence to be expressed. Within a recombinant expression vector "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence. In one embodiment, a vector nucleic acid sequence is a non-natural DNA composite.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

The term "untranslated region" as used herein refers to nucleic acid sequence which will be transcribed by an RNA polymerase but will not be translated into protein by a ribosome. Untranslated regions can be located before or after the open reading frame of a gene, and often modulate transcriptional or translational efficiency. The untranslated region can contain the ribosome binding site (RBS). The strength of the RBS can modulate the rate of ribosome initiation.

The term "promoter region" as used herein refers to the promoter and untranslated region located 5' of the open reading frame. The term "promoter region" as used herein refers to the region located near the transcription start sites of genes, on the same strand and upstream on the DNA (towards the 5' region of the sense strand).

The phrase "transcriptional initiation rate" as used herein, refers to the number of new mRNA molecules produced at a promoter per second. The transcriptional initiation rate is influenced by the polymerase that is transcribing new mRNA, but is generally governed by the strength of the promoter at which transcription is occurring. The stronger the promoter the greater the number of mRNAs that will be produced per second.

The term "polynucleotide" as used herein refers to a nucleic acid (e.g., DNA or RNA) sequence that comprises coding sequences necessary for the production of a polypeptide. The terms "peptide", "polypeptide" and "protein" are used interchangeably to refer to a polymer of amino acid residues. In some embodiments, the terms "peptide", "polypeptide" and "protein" apply to amino acid polymers in which one or more amino acid residue is an unnatural amino acid (UAA).

In some embodiments, the transcriptional initiation rate ranges from 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10 mRNAs per second. In one embodiment, "mRNAs" is mRNA molecules and is used for providing the number of mRNA molecules. Each possibility represents a separate embodiment of the present invention.

In some embodiments, the transcriptional initiation rate is at least 1, 2, 3, 4, 5, 6, 7, 8, 9 mRNAs per second. Each possibility represents a separate embodiment of the present invention. In some embodiments, the transcriptional initiation rate is not more than 10, 9, 8, 7, 6, 5, 4, 3, 2 mRNAs per second. Each possibility represents a separate embodiment of the present invention.

The term "ribosome initiation rate" as used herein, refers to the number of new polypeptides being produced from an mRNA per second. Ribosome binding to the ribosome binding site in the 5' UTR is the major controller of ribosome initiation rate. The stronger the ribosome binding rate the greater the number of new polypeptides that will be produced per second.

In some embodiments, the ribosome initiation rate ranges from 1.0 to 4.5, 1.0 to 4.0, 1.0 to 3.5, 1.0 to 3.0, 1.0 to 2.5, 1.0 to 2.0, 1.0 to 1.5, 1.5 to 4.5, 1.5 to 4.0, 1.5 to 3.5, 1.5 to 3.0, 1.5 to 2.5, 1.5 to 2.0, 2.0 to 4.5, 2.0 to 4.0, 2.0 to 3.5, 2.0 to 3.0, 2.0 to 2.5, 2.5 to 4.5, 2.5 to 4.0, 2.5 to 3.5, 2.5 to 3.0, 3.0 to 4.5, 3.0 to 4.0, 3.0 to 3.5, 3.5 to 4.5, 3.5 to 4.0, 4.0 to 4.5 ribosome per second. Each possibility represents a separate embodiment of the present invention. In some embodiments, the ribosome initiation rate is at least 1.0, 1.5, 2.0, 2.5, 3.0, 3.5, 4.0, 4.5 ribosomes per second. Each possibility represents a separate embodiment of the present invention. In some embodiments, the ribosome initiation rate is not more than 4.5, 4.0, 3.5, 3.0, 2.5, 2.0, 1.5 ribosomes per second. Each possibility represents a separate embodiment of the present invention.

In some embodiments, the open reading frame comprises a TAA as translation stop codon. In some embodiments, the open reading frame comprises a TGA as translation stop codon. In some embodiments, the open reading frame comprises a TAA or a TGA as translation stop codon. In some embodiments, the mRNA transcribed from the open reading frame comprises a UAA as translation stop codon.

In some embodiments, the open reading frame comprises at least one stop codon within the first 240 bases, the first 225 bases, the first 210 bases, the first 195 bases, the first 180 bases, the first 165 bases, the first 150 bases. Each possibility represents a separate embodiment of the present invention.

In some embodiments, the open reading frame comprises at least one stop codon within the first third of the protein, the first quarter of the protein, the first fifth of the protein, the first sixth of the protein. Each possibility represents a separate embodiment of the present invention. In some embodiments, the stop codon is a TAG stop codon.

In some embodiments, a cell is genetically engineered (e.g., transformed, transduced or transfected) with the polynucleotides of the invention or one or more constructs that include one or more polynucleotides of the invention, e.g., a vector of the invention, which can be, for example, a cloning vector or an expression vector. For example, the coding sequences for the orthogonal tRNA, the orthogonal tRNA synthetase, and the polypeptide to be derived are operably linked to gene expression control elements that are functional in the desired host cell. Alternatively, the expression of each of the elements (e.g., orthogonal tRNA orthogonal tRNA synthetase, polynucleotide sequence comprising the unique codon that is recognized by the tRNA, one or more deacetylases or fragments thereof) may be controlled by using an inducible promoter.

In some embodiments, the cell comprises an endogenous genome devoid of all TAG stop codons, and a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises a TAA or TGA as translation stop codon and at least one TAG codon within either the first 240 bases or the first third of the open reading frame.

In some embodiments, the cell comprises an orthogonal translation system comprising an orthogonal tRNA that has an anticodon that corresponds to a stop codon (o-tRNA) and an UAA-specific orthogonal amino-acyl-tRNA synthetase (o-aaRS) and a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises at least one of the stop codon within either the first 240 bases or the first third of the open reading frame.

In some embodiments, the cell comprises an endogenous genome devoid of all TAG stop codons, an orthogonal translation system comprising an orthogonal tRNA that has an anticodon that corresponds to a UAG stop codon (o-tRNA) and an UAA-specific orthogonal amino-acyl-tRNA synthetase (o-aaRS), and a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises a TAA or TGA as translation stop codon and at least one TAG codon within either the first 240 bases or the first third of the open reading frame.

In some embodiments, the cell comprises an endogenous genome devoid of all TAG stop codons, an orthogonal translation system comprising an orthogonal tRNA that has an anticodon that corresponds to a UAG stop codon (o-tRNA) and an UAA-specific orthogonal amino-acyl-tRNA synthetase (o-aaRS), and a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second.

In some embodiments, the cell comprises an endogenous genome devoid of all TAG stop codons, an orthogonal translation system comprising an orthogonal tRNA that has an anticodon that corresponds to a UAG stop codon (o-tRNA) and an UAA-specific orthogonal amino-acyl-tRNA synthetase (o-aaRS), and a vector comprising, a promoter region operably linked to an open reading frame, wherein the open reading frame comprises a TAA or TGA as translation stop codon and at least one TAG codon within either the first 240 bases or the first third of the open reading frame.

In some embodiments, the cell is devoid of release factor 1 (RF1) expression.

Release factor 1 (RF1) is a prokaryotic protein that allows for the termination of translation by recognizing the stop codon in an mRNA sequence. RF1 recognizes TAG and TAA stop codons. In prokaryotes, the RF2 protein also recognizes stop codons, but only the TAA and TGA codons. In some embodiments, the cell is devoid of RF1 expression. Loss of RF1 expression can be achieved, in some embodiments, by removing the gene from the genome of the cell, mutating or removing the regulatory regions, such as the promoter, that control RF1 expression, introducing an agent that silences RF1 expression such as a microRNA, or any one of many techniques for gene ablation that are common in the art.

In some embodiments, the expression of RF1 in the cell is reduced by at least 99%, 95%, 90%, 85%, 80%, 75%. Each possibility represents a separate embodiment of the present invention.

In some embodiments, the cell comprises an endogenous genome devoid of all TAG stop codons and RF1 expression.

In some embodiment, the cell is a cell of the genomically recoded E. coli GRO strain. This cell has all of its endogenous TAG stop codons mutated to TAA stop codons and has the RF1 locus removed from its genome.

In some embodiments, the promoter region comprises the OR2-OR1-Pr promoter region. In some embodiments, the promoter region comprises the lambda repressor promoter such as: OR2-OR1 and/or the following sequence: TGAGCTAACACCGTGCGTGTTGACAATTT-TACCTCTGGCGGTGATAATGGTTGCA (SEQ ID NO: 1) and/or a restriction site such as: GCTAGC (SEQ ID NO: 2), and/or a UTR1 region: AATAATTTTGTTTAACTT-TAAGAAGGAGATATA (SEQ ID NO: 3). In another embodiment, the UTR1 region is derived from the T7 bacteriophage RBS. In another embodiment, the OR2-OR1-Pr promoter region comprises OR2-OR1-Pr-UTR1 and/or P70a-UTR1.

In some embodiments, the restriction site is not present in OR2-OR1-Pr. In some embodiments, the restriction site is a different restriction site, such as is commonly used in the art.

In some embodiments, a mutation is introduced into the OR2-OR1-Pr promoter region. In some embodiments, the mutation is made in the promoter. In some embodiments, the mutation is made in the UTR. In some embodiments, a Thymidine in the promoter is mutated into an adenine. In some embodiments, the promoter region comprises the following sequence: (TGAGCTAACACCGTGCGTGTA-GACAATTTTACCTCTGGCGGTGATAATGGTTGCAG CTAGCAATAATTTTGTTTAACTTTAAGAAGGAGA-TATA) (OR2-OR1-Pr1) (SEQ ID NO: 4). In some embodiments, a guanine in the UTR is mutated into a cytosine. In some embodiments, the promoter region comprises the following sequence:

```
                                           (SEQ ID NO: 5)
(TGAGCTAACACCGTGCGTGTTGACAATTTTACCTCTGGCGGTGATAAT

GGTTGCAGCTAGCAATAATTTTGTTTAACTTTAAGAACGAGATATA)

(OR2-OR1-UTR3).
```

In one embodiment, a sequence is a DNA sequence. In one embodiment, a sequence is a RNA sequence. In one embodiment, a sequence is a protein sequence.

In some embodiments, the cell is for use in producing a protein comprising an UAA. For incorporation of a UAA, free UAA is required such as by incubating a cell in the presence of UAA. In some embodiments, the UAA is Propargyl-l-Lysine. Free Propargyl-l-Lysine may be provided by incubating a bacterial host cell in the presence of Propargyl-l-Lysine.

By another aspect, the present invention concerns a method for producing a protein comprising an unnatural amino acid (UAA), the method comprising: providing at least one cell; expressing in the cell an orthogonal translation system comprising an orthogonal tRNA that has an anticodon that corresponds to a stop codon (o-tRNA) and an UAA-specific orthogonal amino-acyl-tRNA synthetase (o-aaRS) and expressing in the cell a vector comprising, a promoter region operably linked to an open reading frame, wherein the promoter region has a transcriptional initiation rate between 1.0 and 10 mRNAs per second and/or a ribosome initiation rate between 1.0 and 4.5 ribosomes per second and the open reading frame comprises at least one of the stop codon within the first 240 bases or the first third of the open reading frame, and contacting the cell with the UAA, thereby producing the protein comprising the UAA.

In some embodiments, an orthogonal tRNA comprises an anticodon that corresponds to a stop codon (o-tRNA) and an UAA-specific orthogonal amino-acyl-tRNA synthetase (o-aaRS). In some embodiments, a method for producing a protein as described herein is a method for producing a protein comprising an unnatural amino acid. In some embodiments, a method for producing a protein as described herein comprises expressing in the cell a vector comprising, a promoter region operably linked to an open reading frame. In one embodiment, the promoter region comprises a transcriptional initiation rate between 1.0 and 10 mRNAs per second and a ribosome initiation rate between 1.0 and 4.5 ribosomes per second. In one embodiment, the open reading frame comprises at least one of: the stop codon within: (i) the first 240 bases; or (ii) the first third of the open reading frame. In one embodiment, the method comprises contacting the cell with the UAA, thereby producing the protein comprising the UAA.

The term "expressing" as used herein, refers to the biosynthesis of a polynucleotide encoded product, including the transcription and/or translation of the product. Thus, expression of a polynucleotide sequence may refer to transcription of the polynucleotide sequence (e.g., transcription resulting in mRNA or other functional RNA) and/or translation of RNA into a precursor or mature protein (polypeptide).

In some embodiments, the cell is devoid of endogenous TAG stop codons and RF1 expression. In some embodiments, the anticodon corresponds to a UAG stop codon.

By another aspect, the present invention concerns a kit comprising: an orthogonal translation system comprising an orthogonal tRNA that has an anticodon that corresponds to a stop codon (o-tRNA) and an UAA-specific orthogonal amino-acyl-tRNA synthetase (o-aaRS), a vector comprising, a promoter region operably linked to a multiple cloning site (MCS), wherein the promoter region has a transcriptional initiation rate between 1.0 and 10 mRNAs per second and/or a ribosome initiation rate between 1.0 and 4.5 ribosomes per second and instructions for designing a nucleic acid molecule, wherein the nucleic acid molecule comprises at least one of the stop codon within the first 240 bases or the first third of the open reading frame.

The term "multiple cloning site" as used herein refers to a nucleic acid sequence with one or more, two or more, three or more, four or more, five or more, six or more, seven or more, eight or more, nine or more, ten or more DNA restriction enzyme cutting sites such as are commonly used in molecular biology. Each possibility represents a separate embodiment of the present invention.

In some embodiments, the kit is for use in the production of a protein comprising an UAA. In some embodiments, the kit contains the UAA of the orthogonal translation system. In some embodiments, the anticodon corresponds to a UAG stop codon. In some embodiments, the kit further comprises a cell devoid of endogenous TAG stop codons and RF1 expression. In some embodiments, the nucleic acid molecule further comprises a TAA or TGA as a terminal translation stop codon. In some embodiments, the orthogonal translation system is present in a cell provided in the kit.

In some embodiments, the nucleic acid molecule codes for a protein of interest. The term "protein of interest" as used herein refers to virtually any protein which may be of interest to have UAAs integrated therein. Nucleic acid sequences coding for virtually any protein may be used in the vectors and methods of the present application.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "deGFP" as used herein, refers to a variant of the EGFP protein. EGFP refers to enhanced green fluorescent protein as is commonly used in biological research. The deGFP variant was optimized for CFPS Ex/Em: 488/510 nm. In one embodiment, deGFP comprises the following sequence:

(SEQ ID NO: 6)
ATGGAGCTTTTCACTGGCGTTGTTCCCATCCTGGTCGAGCTGGACGGCG

ACGTAAACGGCCACAAGTTCAGCGTGTCCGGCGAGGGCGAGGGCGATGC

CACCTACGGCAAGCTGACCCTGAAGTTCATCTGCACCACCGGCAAGCTG

CCCGTGCCCTGGCCCACCCTCGTGACCACCCTGACCTACGGCGTGCAGT

GCTTCAGCCGCTACCCCGACCACATGAAGCAGCACGACTTCTTCAAGTC

EXAMPLES

Materials and Methods

Bacterial Strains and Plasmids Transformation

E. coli DH5a was used to amplify plasmids and construct deGFP mutants and promoter variants. E. coli C321.ΔA.exp (Addgene strain #49018) was used for expression of deGFP under the OR2-OR1-Pr promoter variants. E. coli BL21 (DE3) was used for the expression of deGFP mutants under the control of T7 promoter. All transformations were done by electroporation using standard protocols. All strains not containing any plasmids were grown in Luria-Bertani (LB) broth (10 g/L NaCl, 10 g/L trypton and 5 g/L yeast extract) overnight at 37° C. for sequential inoculation.

Plasmids and Mutant Construction pBEST-OR2-OR1-Pr-UTR1-deGFP-T500 (Addgene plasmid #40019) plasmid was provided by V.N. deGFP and promoter mutations were introduced by site directed mutagenesis using standard protocols. Primers and reagents used for vector construction can be found in Table 1.

TABLE 1

Primers used for site directed mutagenesis

| Target | Forward primer (SEQ ID NO:) | Reverse primer (SEQ ID NO:) |
|---|---|---|
| deGFP Y35TAG | GCGATGCCACCTAGGGCAAGCTG ACCCTGAA (7) | TTCAGGGTCAGCTTGCCCTAGGTG GCATCGC (8) |
| deGFP D193TAG | CCCCGTGCTGCTGCCCTAGAACC ACTACCTGAGCA (9) | TGCTCAGGTAGTGGTTCTAGGGC AGCAGCACGGGG (10) |
| deGFP Y178TAG | TGCAGCTCGCCGACCACTAGCAG CAGAACACCCCCAT (11) | ATGGGGGTGTTCTGCTGCTAGTG GTCGGCGAGCTGCA (12) |
| OR2-OR1-Pr1 | GCTAACACCGTGCGTGTAGACAA TTTTACCTCTGG (13) | CCAGAGGTAAAATTGTCTACACG CACGGTGTTAGC (14) |
| OR2-OR1-UTR3 | TTGTTTAACTTTAAGAACGAGATA TACCATGGAGCT (15) | AGCTCCATGGTATATCTCGTTCTT AAAGTTAAACAA (16) |

-continued
CGCCATGCCCGAAGGCTACGTCCAGGAGCGCACCATCTTCTTCAAGGAC

GACGGCAACTACAAGACCCGCGCCGAGGTGAAGTTCGAGGGCGACACCC

TGGTGAACCGCATCGAGCTGAAGGGCATCGACTTCAAGGAGGACGGCAA

CATCCTGGGGCACAAGCTGGAGTACAACTACAACAGCCACAACGTCTAT

ATCATGGCCGACAAGCAGAAGAACGGCATCAAGGTGAACTTCAAGATCC

GCCACAACATCGAGGACGGCAGCGTGCAGCTCGCCGACCACTACCAGCA

GAACACCCCCATCGGCGACGGCCCCGTGCTGCTGCCCGACAACCACTAC

CTGAGCACCCAGTCCGCCCTGAGCAAAGACCCCAACGAGAAGCGCGATC

ACATGGTCCTGCTGGAGTTCGTGACCGCCGCCGGGATCTCTAGAGTGCA

CCACCACCACCATCACGTGTAA.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

deGFP Quantification and Purity Assessment deGFP fluorescence was measured during the overnight incubation at 37° C. UAA mutants were supplemented with PrK in a final concentration of 2 mM of UAA. The deGFP mutants were purified using nickel affinity chromatography and the resulting samples were measured using a commercial Bradford assay (Thermo Scientific, Waltham, MA). For western blot, we used goat anti GFP and donkey anti goat (HRP-conjugated) antibodies as primary and secondary antibodies (Santa Cruz, CA, USA), respectively.

deGFP Purification and Mass Spectrometry

For LC-MS validation of incorporation of PrK, nickel affinity chromatography purification of 6×his-tagged deGFP was performed. 100 ml overnight cultures were lysed using BugBuster protein extraction reagent (Novagen, WI, USA) and the 6×His tagged deGFP was purified from the crude lysate using nickel affinity chromatography. The protein-containing eluted fraction was concentrated using a Vivaspin 10 kDa cutoff concentrator (Sartorius, Göttingen, Germany). The resulting concentrated fraction was analyzed by LC-MS (Finnigan Surveyor Autosample Plus/LCQ Fleet, Thermo Scientific, Waltham, MA).

"Click" Reaction and Fluorescent SDS-PAGE deGFP containing PrK was labeled using the Cu(I)-catalyzed azide-alkyne cycloaddition reaction (CuAAC).

The protein sample was resuspended in 0.1 M PB, pH 7.5. Tetramethylrhodamine-azide (Tamra-Az) (Ex/Em 546/565 nm) (Sigma-Aldrich, Rehovot, Israel) was added to a concentration of 100 µM. THPTA, sodium ascorbate and $CuCl_2$ were added to final concentrations of 400 µM, 2.5 mM and 200 µM, respectively. The reaction mixture was incubated at room temperature for 1 hour. A 20 µL sample was diluted with 5×SDS sample buffer and kept for 10 min at 70° C., after which time it was loaded and run on a 4-20% SDS-PAGE gel. Labeled proteins were visualized in-gel using an ImageQuant LAS 4000 imager (Fujifilm, Tokyo, Japan) set in the Cy3 fluorescence mode.

mRNA Quantification

GeneJET RNA purification kit (Thermo Scientific, Waltham, Mass., USA) was used to extract total RNA from bacterial cultures during mid-exponential phase. cDNA samples were synthesized from RNA samples using iScript cDNA synthesis kit (Biorad, Hercules, Calif., USA). qPCR was performed using KAPA SYBR® FAST qPCR Kit (KapaBiosystems, Wilmington, Mass., USA) with the recommended relative calibration curve protocol, in StepOne-Plus Real-Time PCR System (Thermo Scientific, Waltham, Mass., USA). The primers found in Table 2 were used for the Real-Time quantification, 16S rRNA was used as the standard:

TABLE 2

Primers used for Real Time quantification of mRNA expression

Figure 1B:
Figure 1C:
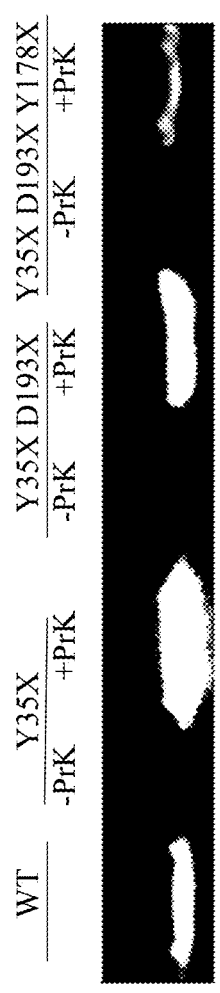

| Target | Forward primer (SEQ ID NO:) | Reverse primer (SEQ ID NO:) |
| --- | --- | --- |
| deGFP | ATGAAGCAGCACGACTTCTT (17) | GTGGCTGTTGTAGTTGTACTC (18) |
| 16S rRNA | CGGTGAATACGTTCCCGG (19) | GGTTACCTTGTTACGACTT (20) | thogonal such that only proteins containing PrK that underwent the click reaction with the fluorophore produce a fluorescent band upon excitation at 546 nm on an SDS-PAGE (FIG. 1B). It could also be seen that an increase in fluorescence correlates with the increase in the number of incorporated UAAs into the protein, corresponding to the number of fluorescent dye molecules attached to each protein molecule. In the Western blot analysis (FIG. 1C) performed after loading a gel with the crude lysates of each mutant and upon blotting and using anti-GFP antibody, we could see a clear band corresponding to deGFP in cultures grown in the presence of PrK (~26.5 kDa). On the other hand, when the same cultures were grown in the absence of UAA, there was no detectable band of deGFP on either the fluorescent gel (565 nm) or a Western blot, indicating that there is no misincorporation of other amino acids instead of the UAA, confirming the results of GFP fluorescence shown in FIG. 1A. As expected, WT deGFP shows a band only in the Western blot analysis and not in the fluorescent gel, due to a different fluorescence spectrum between the fluorophore and deGFP and the fluorescence channel that was used to detect fluorescence. ESI-MS analysis of affinity-purified proteins confirmed the incorporation of PrK in all deGFP mutants (FIG. 6A-E).

Example 1

A Strong Promoter Region Drives Expression of deGFP with UAAs

To test the efficiency of the OR2-OR1-Pr synthetic promoter region in combination with the use of the GRO strain for the production of proteins containing UAAs, we first tested the expression of deGFP (an EGFP variant optimized for CFPS Ex/Em: 488/510 nm) (SEQ ID NO: 6), with its gene modified to contain one, two or three TAG stop codons encoding for the site-specific incorporation of the Pyrrolysine derivative: Propargyl-1 Lysine (PrK). In order to estimate the amounts of protein produced for each mutant, fluorescence of deGFP during bacterial growth was measured (FIG. 1A). The results show high levels of protein expression that decrease as we add more TAG mutations into the protein. This decrease in fluorescence was correlated with an increase in instability of mRNA (vide infra) and the efficiency as well as availability of the UAA incorporation machinery (i.e. the OTS). When mutants were grown in the absence of UAA in the growth media, only background fluorescence from the medium was observed, similar to that of the control culture of the GRO strain without any plasmids.

Figure 5:
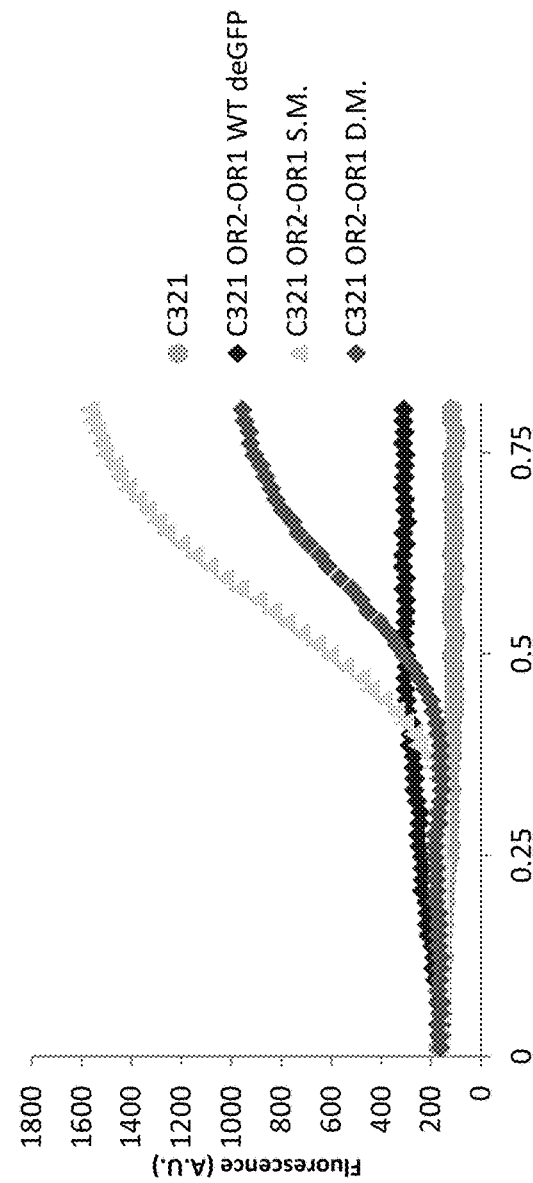
FIG. 5: deGFP fluorescence during incubation at 30° C. A line graph of deGFP fluorescence of the different mutants during incubation at 30° C. UAA mutants were supplemented with 2 mM PrK per UAA mutation. S.M.—single mutant (Y35TAG), D.M.—Double mutant (Y35TAG D193 TAG).
Figure 6A:
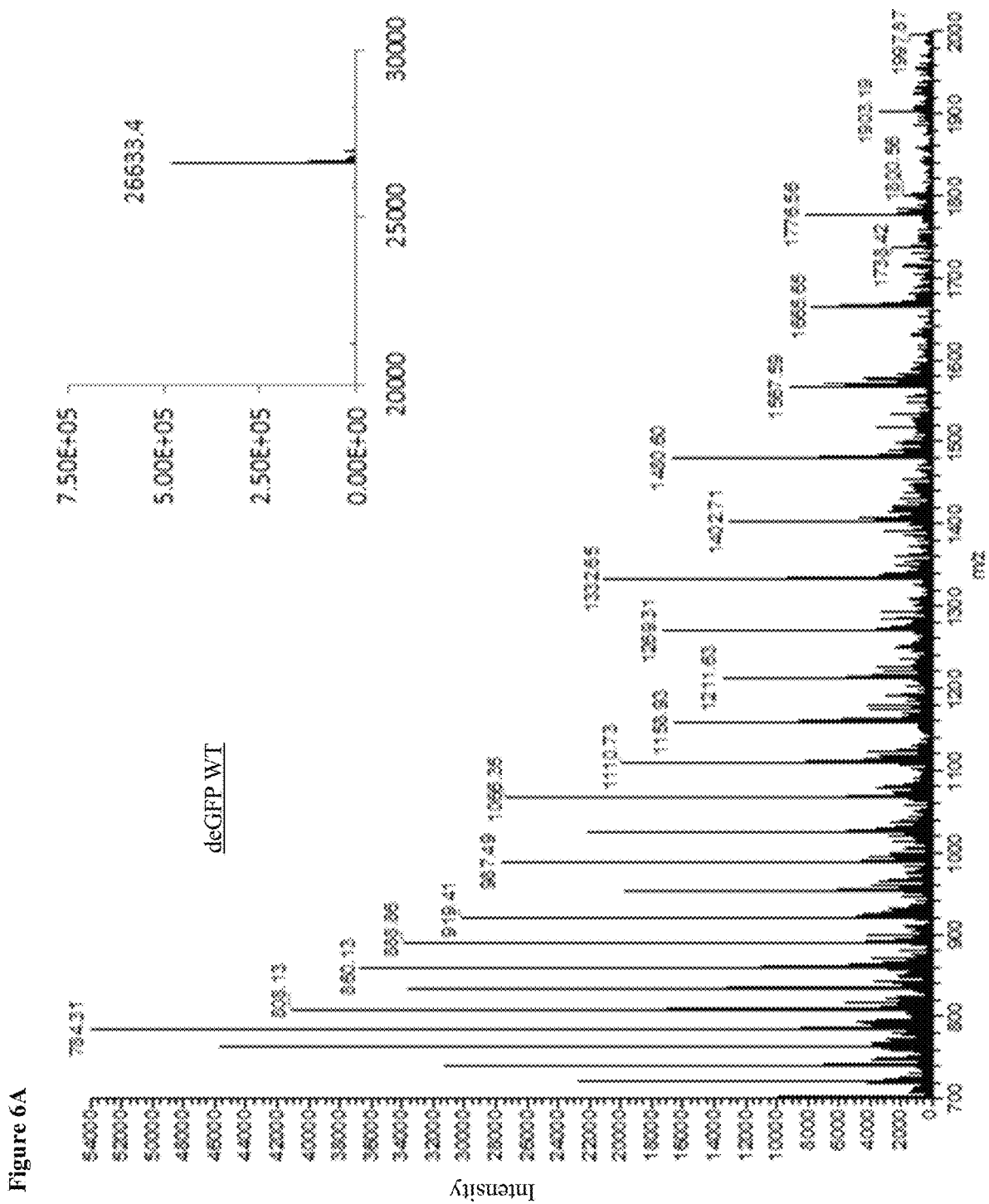
FIGS. 6A-E: MS Spectrums. A readout of an ESI-MS analysis of WT deGFP and the deGFP mutants. Calculated masses of deGFP WT: 26634Da; Y35PrK: 26680Da; D193PrK: 26728.4Da, Y35D193PrK: 26776Da; Y35l D193Y178: 26822Da, Insets show the deconvoluted spectrum.
Figure 6B:
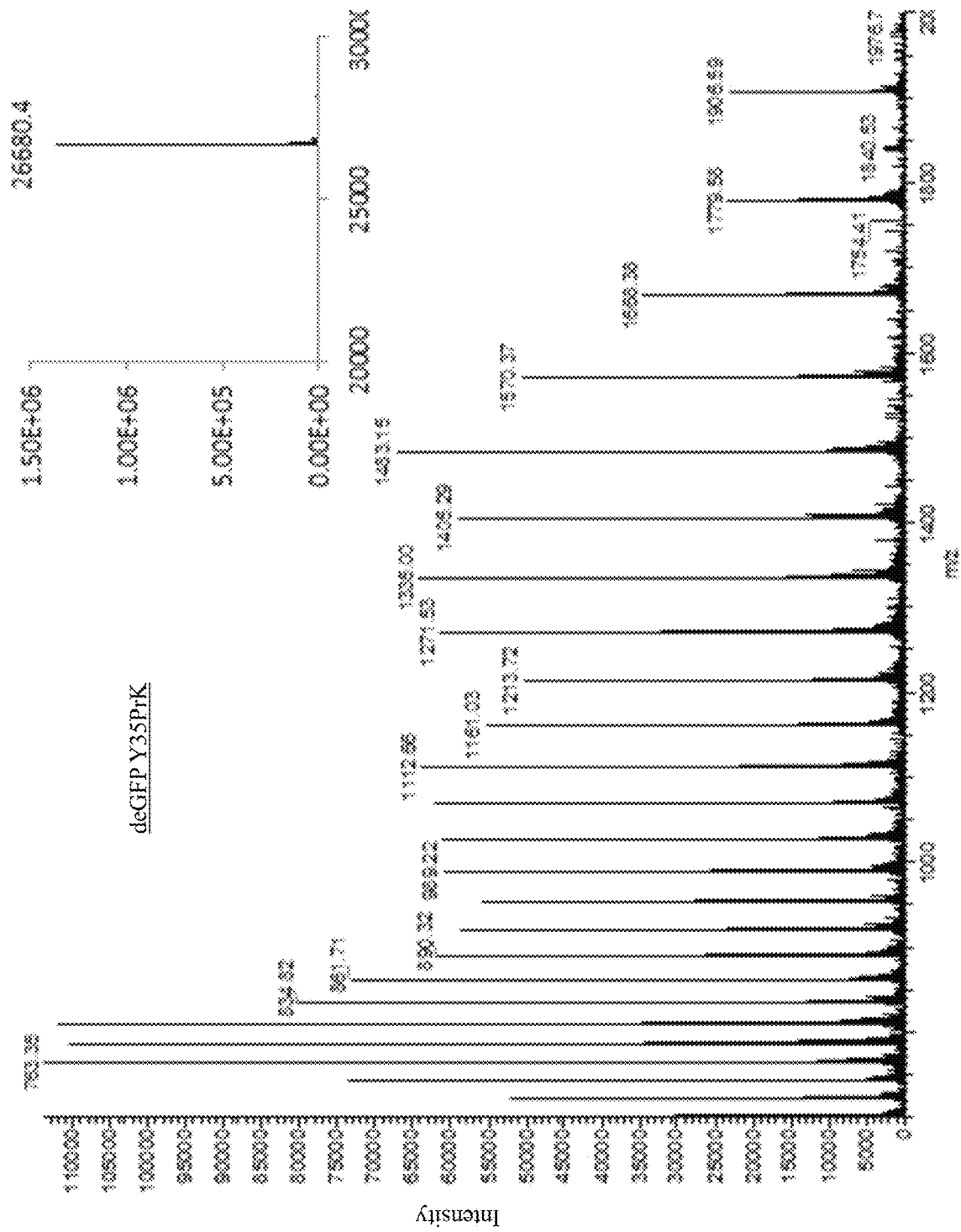
Figure 6C:
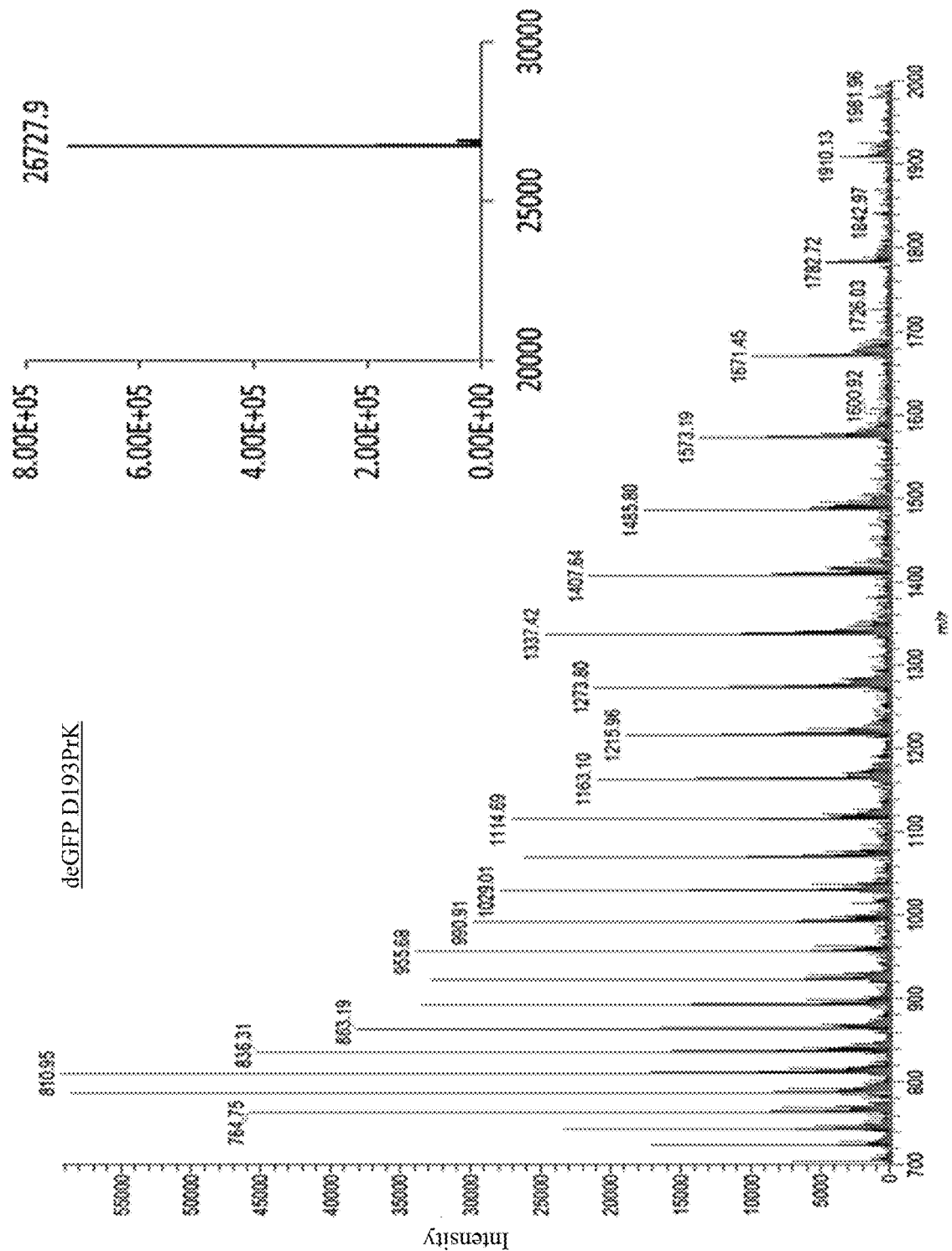
Figure 6D:
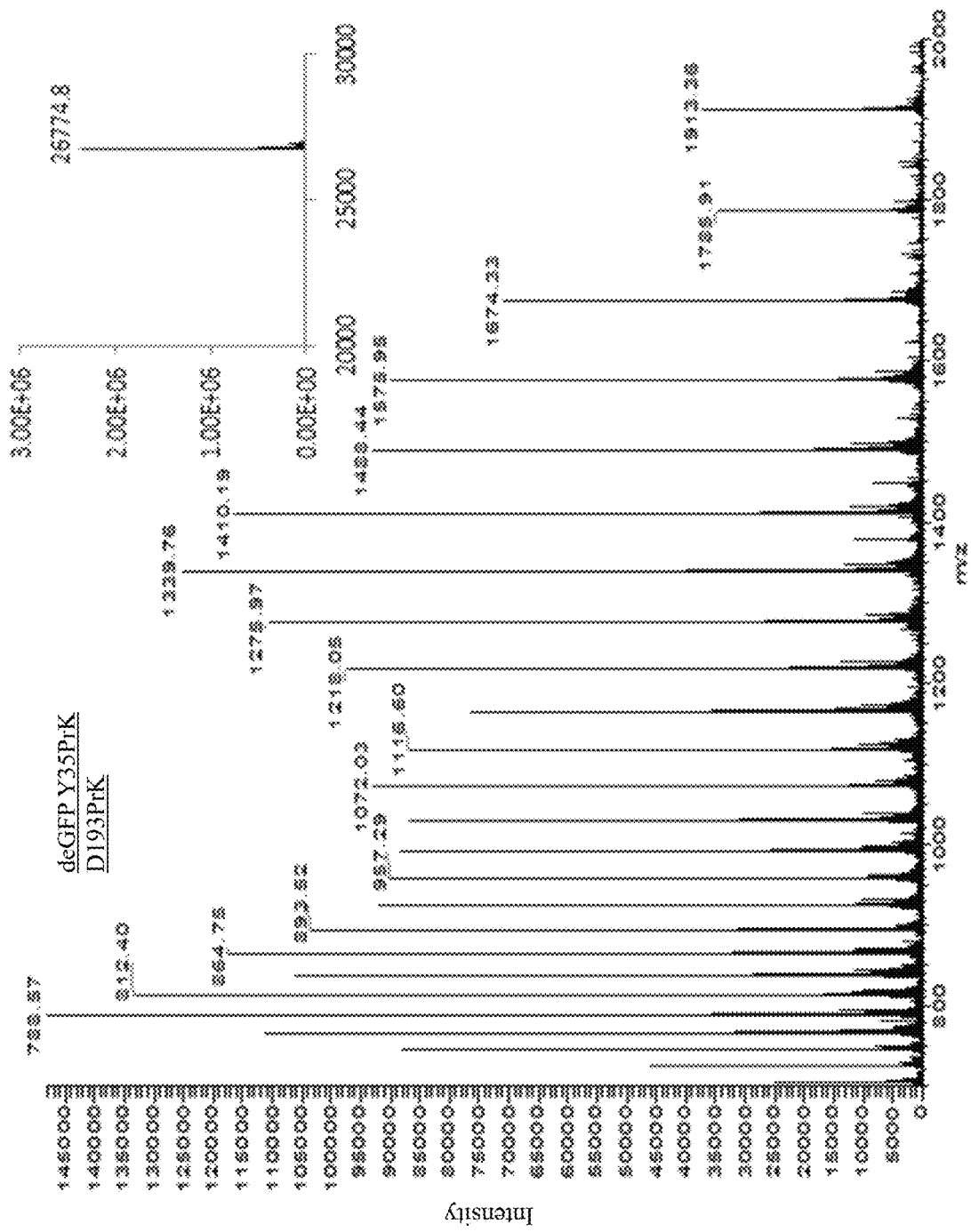
Figure 6E:
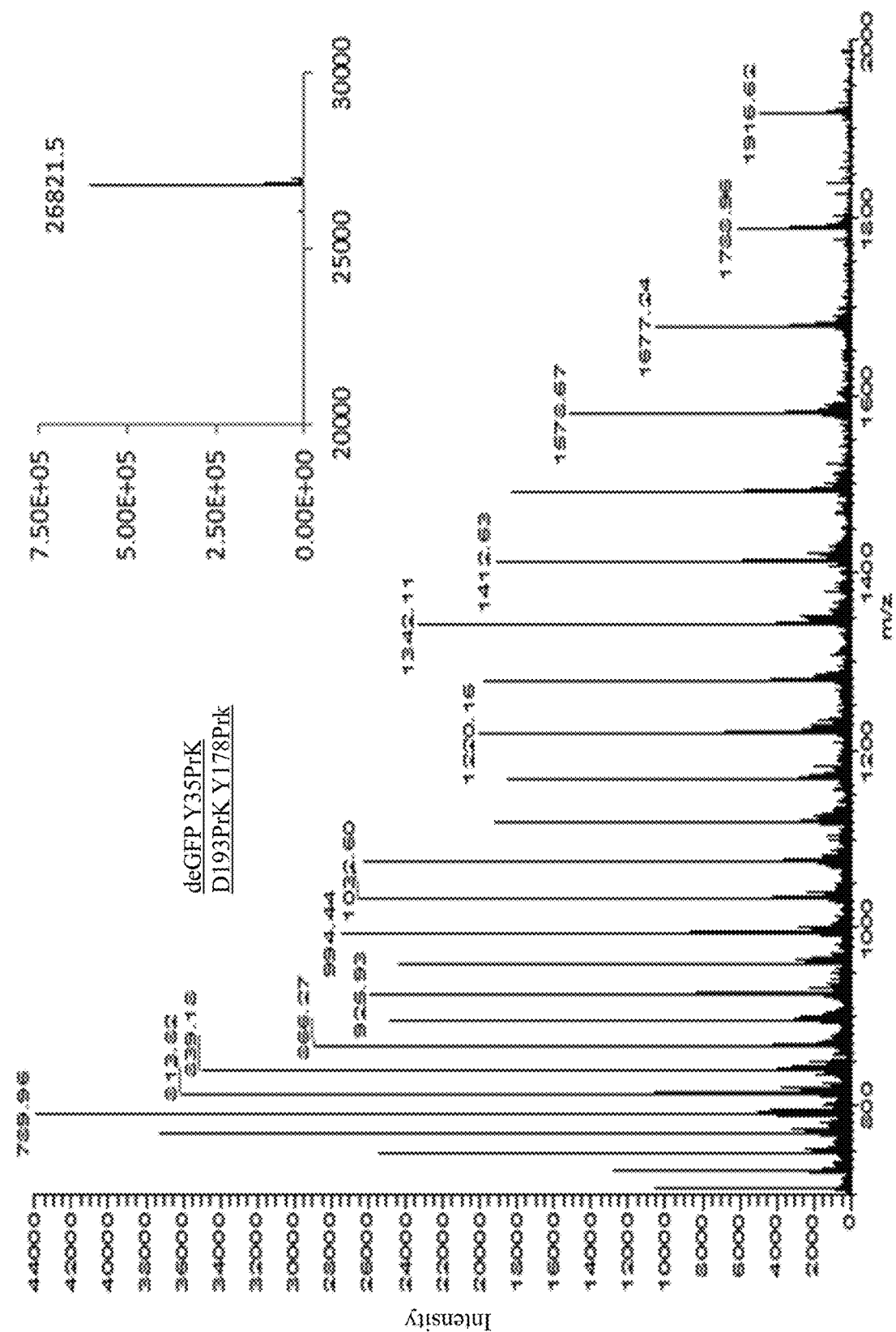

In order to detect the presence of the UAA in the expressed protein, crude lysates containing deGFP with site specifically incorporated PrK were reacted with azide modified fluorescent marker (Ex/Em 546/565 nm) through copper (I) catalyzed azide-alkyne cycloaddition reaction ("click reaction"). The reaction between the alkyne group on the Propargyl-l-Lysine and the azide-fluorophore is bio-or- Interestingly, when expressing WT deGFP, very little to no deGFP was detected—presumably due to toxicity caused by the overexpression of the protein and the accumulation of incompletely folded protein. GFP maturation can be a rather long process, as described by Heim and coworkers (Heim R, et al. Proceedings of the National Academy of Sciences of the USA 1994, 91: 12501-4). The process requires the presence of oxygen and protein accumulates in the cell when unfolded, which may result in non-fluorescent protein in the soluble fraction and in inclusion bodies. One of the common methods used for preventing the formation of inclusion bodies is expression at lower temperatures (e.g. 30° C.). When we tried to overexpress WT deGFP at lower temperatures we saw no improvement in fluorescence levels (FIG. 5). The problem with this method is that it slows down all processes in the host cell, including bacterial growth, protein maturation and the activity of other enzymes.

Example 2

Reduced Promoter Strength Drastically Reduces Production of deGFP with UAAs

Figure 2A:
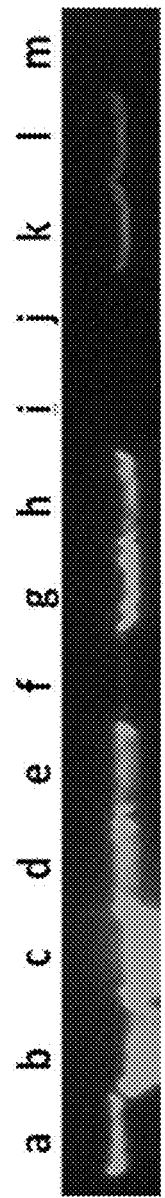
FIGS. 2A-B: Western blot analysis of deGFP mutants with different promoter variants and comparison to the pET system. (2A) An image of a Western blot of crude lysates of C321 deGFP mutants. (a) OR2-OR1-Pr deGFP WT, (b) OR2-OR1-Pr1 deGFP WT, (c) OR2-OR1-Pr-UTR3 deGFP WT, (d) OR2-OR1-Pr Y35PrK, (e) OR2-OR1-Pr1 Y35PrK, (f) OR2-OR1-Pr-UTR3 Y35PrK, (g) OR2-OR1-Pr Y35D193PrK, (h) OR2-OR1-Pr1 Y35D193PrK, (i) OR2-OR1-Pr-UTR3 Y35D193PrK, (j) OR2-OR1-Pr Y35D193Y178 w/o PrK, (k) OR2-OR1-Pr Y35D193Y178 PrK, (l) OR2-OR1-Pr1 Y35D193Y178PrK, (m) OR2-OR1-Pr-UTR3 Y35D193Y178PrK. (2B) An image of a Western blot comparison of deGFP mutants' expression in OR2-OR1 system and pET system: (a) C321 bacteria w/o plasmid, (b) OR2-OR1-Pr deGFP WT, (c) OR2-OR1-Pr-UTR3 deGFP WT, (d) OR2-OR1-Pr Y35 w/o PrK, (e) OR2-OR1-Pr Y35PrK, BL21 pET15b-deGFP WT, (g) BL21 pET15b-Y35 w/o PrK, (h) BL21 pET15b-Y35PrK.

We hypothesized that a weaker promoter region would decrease the toxic effect of protein overexpression, and produce larger amounts of active WT deGFP. As weaker variants of the promoter region, we used promoter regions with single mutations in the promoter of OR2-OR1-Pr as well as in the UTR region, named OR2-OR1-Pr1 (SEQ ID NO: 4) and OR2-OR1-Pr-UTR3, (SEQ ID NO: 5) respectively. We calculated that OR2-OR1-Pr1 and OR2-OR1-Pr-UTR3 variants are 4 and 5 times weaker than the original OR2-OR1-Pr promoter (data not shown). The relative promoter strength was determined by the protein expression levels with the different variants in-vitro. We compared the fluorescence generated by cultures harboring WT deGFP under the control of the different variants of the OR2-OR1-Pr promoter region. We observed greater quantities of deGFP than when we used the weaker OR2-OR1-Pr1 and OR2-OR1-UTR3 promoter regions (FIG. 2A). The opposite trend was observed when using the promoter variants with the TAG mutants, where lower quantities of protein were detected when using the weaker promoter variants.

Figure 2B:
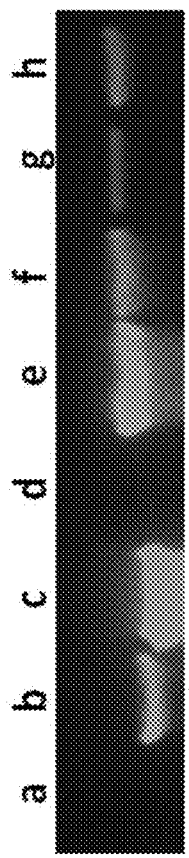

We compared our system to one of the most widely used commercial overexpression systems the pET system (Novagen, WI, USA), which is based on the T7 bacteriophage promoter (pET manual, Novagen). The system depends on a T7 RNA polymerase (T7 RNAP), which is inserted in the genome of the host organism under the control of the lac promoter. The target protein expression is controlled by the addition of lactose/IPTG to the growth medium as an inducer, which promotes the production of the T7 RNAP and subsequent expression of the target protein. The pET plasmid contains the target gene under the control of the T7 promoter and the laI gene that produces the repressor for the lac promoter to prevent the expression of the T7 RNAP in the absence of an inducer. There are several disadvantages in this system: first, the necessity for the presence of the T7 RNAP cassette in the host's genome means that only certain strains may be used with this system. Second, protein induction was shown to be an all-or-non process at the cellular level (Novick and Weiner, 1957), meaning that in a culture induced in sub-saturation inducer concentration some of the cells are fully induced and others are not induced at all. This creates an advantage to the un-induced cell over the induced ones in a culture such that the un-induced cell grows faster, eventually taking over the culture, compared to the induced cell, which suffer from the toxic effect of the protein overexpression. Comparing our system with the expression of deGFP harbored in the pET15b plasmid, we observed much higher yields both for WT and for the single TAG mutant while the double mutant expressed in the pET system showed no detectable deGFP expression. Furthermore, in the pET15b system, when the single TAG mutant was grown in the absence of PrK in the medium, we noticed deGFP expression levels that were very close to those of PrK supplemented culture. These results suggest that there are very high levels of misincorporation (read-through) of natural amino acids into the UAA designated site (FIG. 2B).

Example 3

Early Insertion of UAAs is Required for Protein Production

Figure 3:
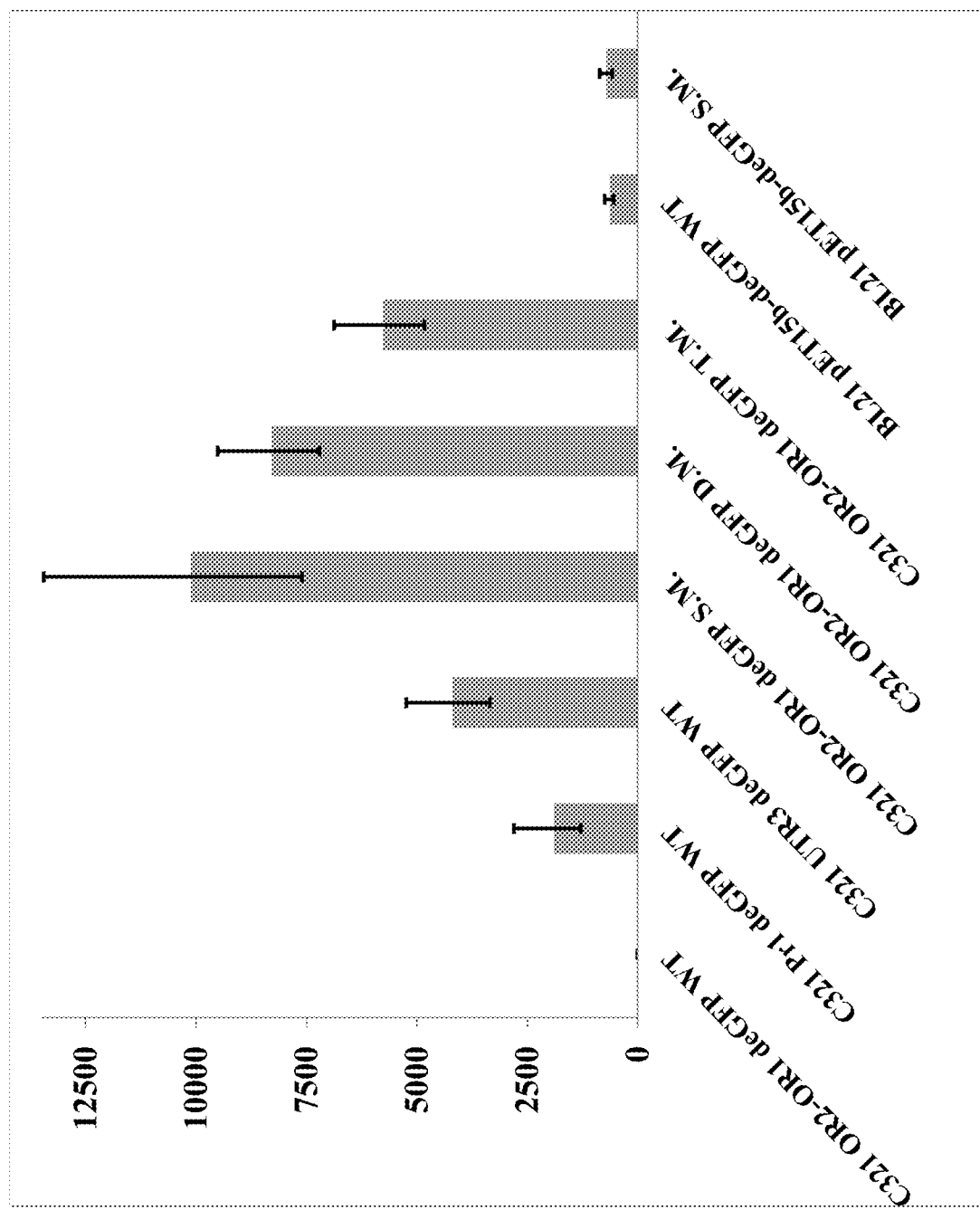
FIG. 3: deGFP mRNA quantification using qPCR. A bar chart, showing the relative quantity (RQ) of deGFP mRNA for each mutant that exist during middle of deGFP expression phase. Results are normalized to OR2-OR1 WT deGFP. S.M., D.M. and T.M. are single double and triple mutants, respectively.
Figure 4:
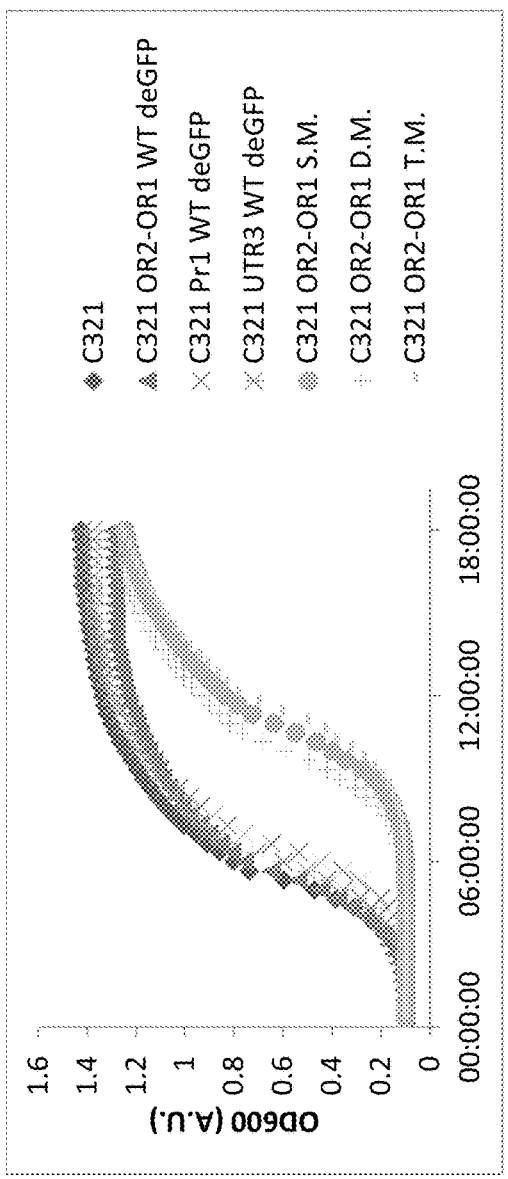
FIG. 4: Growth curve of the different mutants. A growth curve chart depicting $OD_{600}$ of the different mutants during incubation at 37° C. UAA mutants were supplemented with 2 mM PrK per UAA mutation. S.M.—single mutant (Y35TAG), D.M.—Double mutant (Y35TAG D193TAG), T.M.—Triple mutant (Y35TAG D193TAG Y178TAG).

In order to determine the source of the observed opposite trends of protein expression between the WT and TAG mutants, we quantified deGFP mRNA levels in each mutant using gene specific primers, and correlated it with the protein expression levels (FIG. 3). The results show the same trend that was observed for the protein quantification assays. For the different promoter variants preceding the encoded WT deGFP gene, mRNA concentrations in the sample was greater in the case of a weaker promoter variant. When expressing deGFP PrK mutants with the OR2-OR1-Pr promoter, we observed smaller amounts of mRNA with the addition of TAG codons into the messenger—corresponding to more sites of UAAs incorporation into the protein. The results also show very low mRNA levels in a BL21 cell expressing deGFP through the pET system, compared to the OR2-OR1-Pr promoter used in GRO strain. The results support the hypothesis that overexpression of deGFP and accumulation of unfolded intermediates in the cell trigger a feedback loop that decreases the transcription process as well as mRNA maturation. In WT deGFP, the weaker the promoter, the lower the toxicity effects of unfolded intermediates and the more protein produced.

Figure 7:
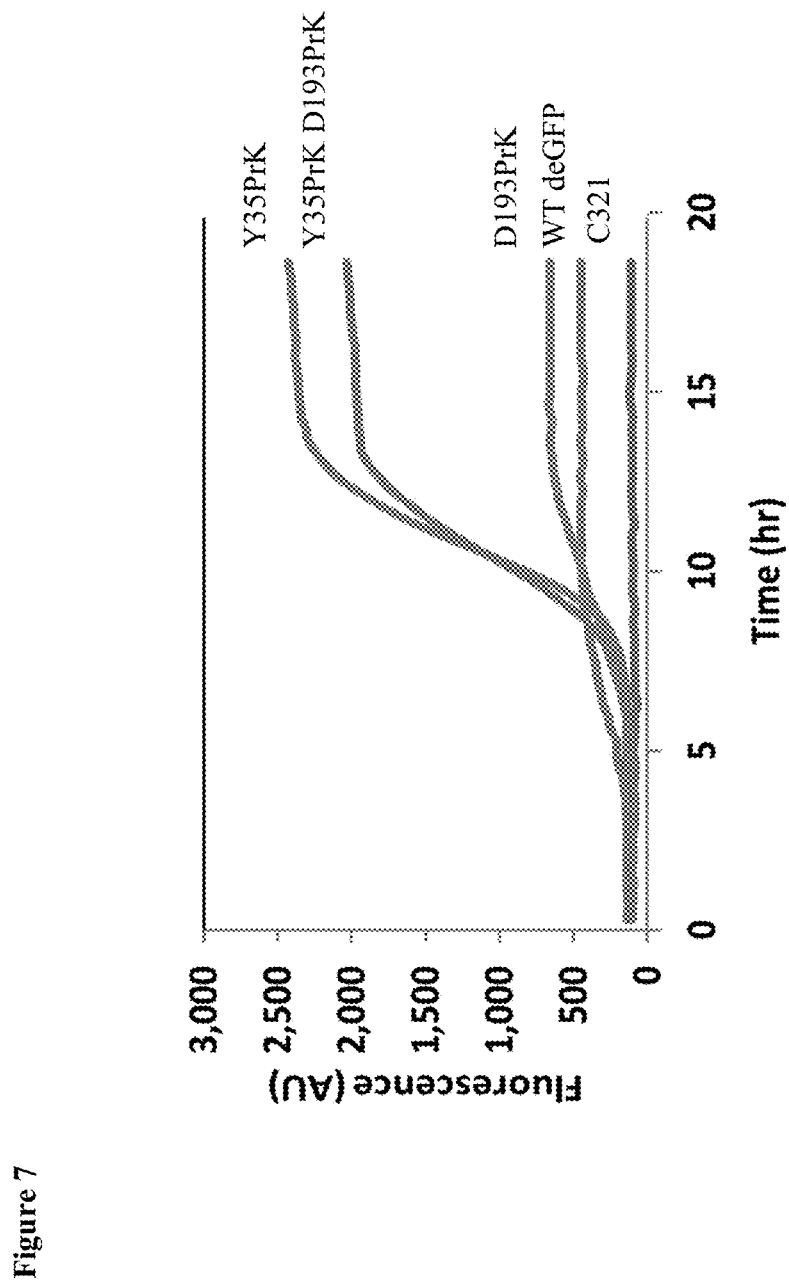
FIG. 7: The 'rescue effect' caused by early UAA incorporation. A line chart, measuring the deGFP fluorescence during bacterial growth of C321 expressing WT deGFP, Y35PrK mutant, D193PrK mutant, Y35PrK D193PrK double mutant and the background fluorescence of the bacteria. Only incorporation of the UAA early in the polypeptide resulted in significant protein expression.

Every codon has a different elongation rate, but the entire set of bacterial codons can be divided into three groups based on translation rate—fast (A), medium (B) and slow (C)—which correspond to elongation rates of 35, 8 and 4.5 codons per second, respectively (Mitarai N. et al. Physical Biology 2013, 10(5): 056011). The non-canonically translated UAG codon was assigned a new translation rate category, group (D), which had a significantly lower elongation rate of 0.04 codons per minute. Since the UAA incorporation mechanism slows down the translation process considerably, it avoids the accumulation of unfolded intermediates and the toxic effect associated with them. When more stop codons are added to the gene, the mRNA becomes more unstable (shorter lifetime), leading to a lower concentration of mRNA in the cell (FIG. 3). The lower mRNA concentrations coincide with the protein levels found for each of the mutants. Interestingly, the effect of UAA incorporation was found to have a positional bias. UAA was incorporated into deGFP within the first third of the amino acid sequence at position 35 (Y35PrK), and also at a much later position (D193PrK). When inserted early in a nascent peptide, UAA incorporation led to robust protein expression whereas late insertion resulted in very minimal expression (FIG. 7). A double mutant still produced robust expression as the toxic effect was mitigated by the early UAA, although slightly lowly protein levels were observed likely due to the reduction in mRNA that was previously discussed.

The comparison of mRNA levels between OR2-OR1-Pr and pET systems, also correlates with the protein expression levels discussed previously. Because each protein has a unique post translation processing and folding mechanisms, it is crucial to assign to each protein a suitable promoter that will produce the highest amounts of biologically functional protein. We assume that proteins with faster and less complicated maturation process will be expressed at larger concentrations by stronger promoter variants and vice-versa. We have shown that our ability to control the expression level by altering the strength of the promoter is a powerful tool that allows considerable improvement of the overexpression of very large amounts of recombinant proteins, by avoiding toxicity for the host organism.

Our modified promoter combined with the recoded GRO strain yield unprecedented amounts of protein with up to 3 incorporated UAAs, with no detectable background of misincorporation. The maximum yields achieved using this system were up to 352 mg/L culture of the WT deGFP protein under the control of the OR2-OR1-Pr-UTR3 promoter variant. PrK containing protein yields were up to 34.2, 19.1 and 4.8 mg protein/L for the single, double and triple mutants, respectively. The ability to adjust the promoter strength according to the target protein enables achieving high yields with proteins of different complexity. The strength of the OR2-OR1-Pr promoter is well calibrated to the UAA incorporation machinery so that larger yields of mutant proteins with multiple UAAs are produced. This system is very promising as it shows superior results in terms of protein yields as well as in UAA incorporation fidelity and efficiency, compared to the widely-used pET system. In general, our research demonstrates that it is indeed beneficial and possible for the user to fine-tune the strength of promoter according to the specific protein expressed.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

The invention claimed is:

1. A cell, comprising:
   a) an orthogonal translation system comprising an orthogonal tRNA, said orthogonal tRNA comprises an anticodon that corresponds to a stop codon (o-tRNA) and an unnatural amino acid (UAA)-specific orthogonal amino-acyl-tRNA synthetase (o-aaRS), and b) a vector comprising, a promoter region operably linked to an open reading frame, wherein said promoter region comprises a OR2-OR1-Pr promoter and said open reading frame comprises at least one of said stop codon located within: (i) the first 240 bases; or (ii) the first third of the open reading frame.

2. The cell of claim 1, wherein said UAA is Propargyl-l-Lysine (PrK).

3. The cell of claim 1, wherein said stop codon is a TAG stop codon.

4. The cell of claim 1, wherein said cell is devoid of release factor 1 (RF1) expression.

5. The cell of claim 1, wherein said cell further comprises an endogenous genome devoid of a TAG stop codon.

6. The cell of claim1, wherein said cell is a genomically recoded E. coli (GRO) strain and said stop codon is a TAG stop codon.

7. The cell of claim 1, wherein said OR2-OR1-Pr promoter region consists of, from 5' to 3', SEQ ID NO: 1, and SEQ ID NO: 2.

8. A method for producing a protein comprising an unnatural amino acid, comprising:
   a) providing at least one cell of claim 1;
   b) expressing in said cell the orthogonal translation system comprising the orthogonal tRNA, said orthogonal tRNA comprises the anticodon that corresponds to the stop codon (o-tRNA) and the UAA-specific orthogonal amino-acyl-tRNA synthetase (o-aaRS);
   c) expressing in said cell the vector comprising, the promoter region operably linked to the open reading frame, wherein said promoter region comprises the OR2-OR1-Pr promoter and said open reading frame comprises at least one of: said stop codon within: (i) the first 240 bases; or (ii) the first third of the open reading frame; and
   d) contacting said cell with said UAA, thereby producing said protein comprising said UAA.

9. The method of claim 8, wherein said UAA is Proparagyl-l-Lysine.

10. The method of claim 8, wherein said stop codon is a TAG stop codon.

11. The method of claim 8, wherein said cell is devoid of RF1 expression.

12. The method of claim 8, wherein said cell is devoid of said TAG stop codon.

13. The method of claim 8, wherein said cell is a genomically recoded E. coli (GRO) strain.

14. The method of claims 8, wherein said stop codon is a TAG stop codon.

15. The method of claim 8, wherein said promoter region comprises an OR2-OR1-Pr promoter region.

16. The cell of claim 1, wherein said vector further comprises a 5' untranslated region (UTR) 3' to said promoter region and wherein said 5' UTR comprises SEQ ID NO: 3.

17. A kit comprising:
   a) an orthogonal translation system comprising an orthogonal tRNA, said orthogonal tRNA comprises an anticodon that corresponds to a stop codon (o-tRNA) and an UAA-specific orthogonal amino-acyl-tRNA synthetase (o-aaRS);

b) a vector comprising a promoter region operably linked to a multiple cloning site (MCS), wherein said promoter region comprises a OR2-OR1-Pr promoter and has a transcriptional initiation rate between 1.0 and 10 mRNAs per second and a ribosome initiation rate between 1.0 and 4.5 ribosomes per second;

c) instructions for designing a nucleic acid molecule, wherein said nucleic acid molecule comprises at least one of said stop codon within: (i) the first 240 bases; or (ii) the first third of the open reading frame.

18. The kit of claim 17, further comprising said UAA, a cell devoid of a TAG stop codon and devoid of RF1 expression or both.

19. The kit of claim 17, wherein said stop codon is a TAG stop codon.

* * * * *